United States Patent [19]

Prat Quiñ et al.

[11] Patent Number: 5,502,237
[45] Date of Patent: Mar. 26, 1996

[54] 1-ARYLOXY-3-ALKYLAMINO-2-PROPANOL-NITRATE ESTERS, THE USE THEREOF AND CORRESPONDING PHARMACEUTICAL COMPOSITION

[75] Inventors: María Prat Quiñ, Barcelona; Joan Pi Sallent, La Llagosta; Dagmar V. Veit, Saint Joan Despi, all of Spain

[73] Assignee: Prodesfarma, S. A., Barcelona, Spain

[21] Appl. No.: 265,960

[22] Filed: Jun. 27, 1994

[30] Foreign Application Priority Data

Jul. 30, 1993 [ES] Spain ................... 9301721

[51] Int. Cl.$^6$ ................... C07C 205/01
[52] U.S. Cl. ................ 560/21; 560/23; 560/156; 564/165; 568/583; 568/587; 568/592
[58] Field of Search ............. 560/156, 21, 23; 568/583, 587, 592; 564/165; 514/509

[56] References Cited

U.S. PATENT DOCUMENTS 3,873,600   3/1975   Brandstrom et al. ............ 514/509

FOREIGN PATENT DOCUMENTS 0034461   8/1981   European Pat. Off. .
0053435   9/1986   European Pat. Off. .

*Primary Examiner*—José G. Dees
*Assistant Examiner*—Dwayne C. Jones
*Attorney, Agent, or Firm*—McAulay Fisher Nissen Goldberg & Kiel

[57] ABSTRACT

The 1-aryloxy-3-alkylamino-2-propanol nitrate esters of general formula I

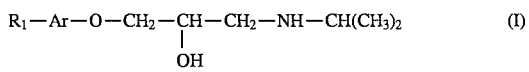

the enantiomers and diastereoisomers and the therapeutically acceptable salts thereof wherein $R_1$ is a chain of general formula II— $(CH)_m$—Z—$R_2$, where: m is 1 or 2; Z is an —O— ether, —CONH-amide or —COO— ester function; and $R_2$ is a $C_{2-3}$ straight or branched chain alkyl having at least one —$ONO_2$ group as a substituent; and Ar is a benzene ring when Z is the ether or ester function, and a naphthalene ring when Z is the amide function, are of use for the treatment of cardiovascular affections.

3 Claims, No Drawings

1-ARYLOXY-3-ALKYLAMINO-2-PROPANOL-NITRATE ESTERS, THE USE THEREOF AND CORRESPONDING PHARMACEUTICAL COMPOSITION

BACKGROUND OF THE INVENTION

1. Field of the Invention

The present invention relates to 1-aryloxy-3-alkylamino-2-propanol nitrate esters of general formula I

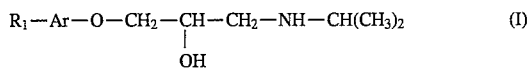  (I)

to the enantiomers and diastereoisomers and the therapeutically acceptable organic and inorganic acids salts thereof; where $R_1$ is a chain of general formula II $$-(CH_2)_m-Z-R_2 \quad (II)$$

where: m is 1 or 2; Z is an —O— ether, —CONH amide or —COO— ester function; and $R_2$ is a $C_{2-3}$ straight or branched chain alkyl having at least one nitroxy group as substituent; and Ar is a benzene ring when Z is the ether or ester function, and a naphthalene ring when Z is the amide function.

SUMMARY OF THE INVENTION

As stated above, the invention relates also to therapeutically acceptable organic and inorganic acid salts of general formula I compounds, such as hydrochlorides, maleates, fumarates, oxalates, succinates, etc.

The following formula I compounds are of particular interest:

1-isopropylamino-3-[4-(2-nitroxy)ethoxymethyl]phenoxy-2-propanol, 1-isopropylamino-3-[4-(3-nitroxy)propoxymethyl]phenoxy-2propanol, 1-isopropylamino-3-[4-(2,3-dinitroxy)propoxymethyl]phenoxy-2-propanol, 1-(2-hydroxy-3-isopropylamino)propoxy-N-(2-nitroxyethyl)-2naphthalene acetamide, 2-(2-hydroxy-3-isopropylamino)propoxy-N-(2-nitroxyethyl)-1-naphthalene acetamide, 2-nitroxyethyl 4-[(2-hydroxy-3-isopropylamino)propoxy]phenyl acetate.

DESCRIPTION OF THE PREFERRED EMBODIMENTS

One process for the preparation of these compounds, when the ether or amide function is present in $R_1$, consists of reacting a phenyl derivative of general formula III $$R_1-Ar-OH \quad (III)$$

where $R_1$ and Ar have the same meanings as in general formula I with an epihalohydrin of general formula IV

  (IV)

where X may be chlorine or bromine, in an aqueous or hydroalcoholic medium, in the presence of a base, preferably an alkali hydroxide, to form the epoxide of general formula V

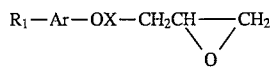  (V)

where $R_1$ and Ar have the same meanings as in general formula I, which is finally reacted with isopropylamine VI

  (VI)

in an inert polar organic, preferably alcoholic, medium to give compounds of general formula I.

The intermediates of general formula III, the preparation of which is not described in this patent, may nevertheless be easily prepared by conventional synthesis processes.

Where $R_1$ contains an ether function, the starting products may be a hydroxyphenyl alcohol and a glycol (GB 1,041,554; U.S. Pat. No. 4,258,062) to give a hydroxyphenylalkoxy alcohol which is treated with fuming nitric acid and acetic anhydride, after acetylation in an alkaline medium, to introduce the nitroxy function (EP 0 034 461).

The product is finally deacetylated by gentle hydrolysis with sodium bicarbonate in a hydroalcoholic medium (J. Am. Chem. Soc. 93, 746 (1971). See the following scheme:

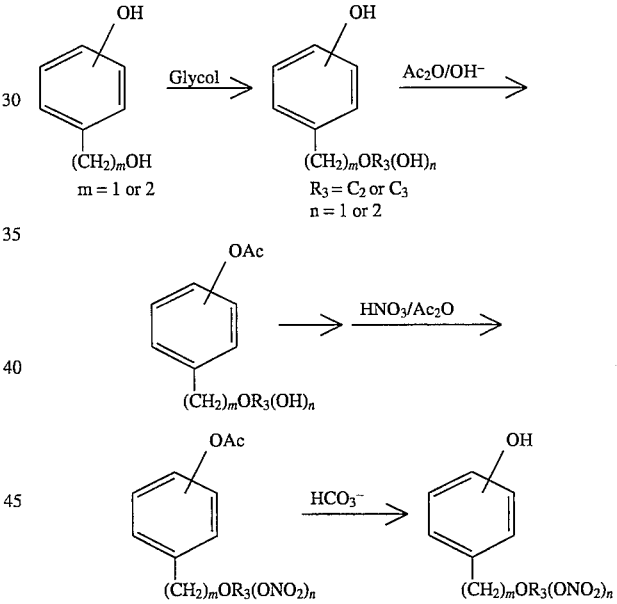

Where $R_1$ contains an amide function, the starting product may be a hydroxynaphthylalkylcarboxylic acid, which is acetylated in an alkaline medium, is reacted with a nitroxyalkylamine (Bull. Soc. Chim. Fr. 470 (1944) with the aid of a gentle condensation agent, such as 1,1'-carbonyl diimidazole or DDC. It is finally deacetylated with sodium bicarbonate in a similar way as described for the ether, as per the following scheme:

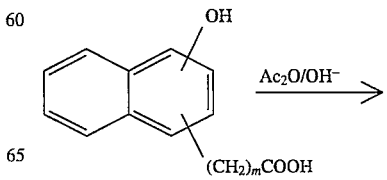

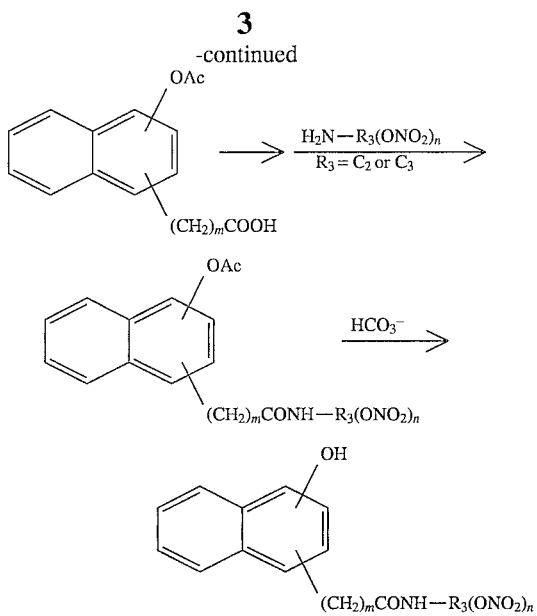

Where $R_1$ contains an ester function, these compounds may be synthesized starting from derivatives of general formula VII, the synthesis of which is described in the literature (EP-A-O 237 239 )

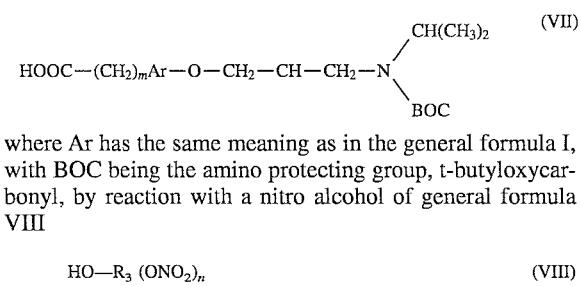

where Ar has the same meaning as in the general formula I, with BOC being the amino protecting group, t-butyloxycarbonyl, by reaction with a nitro alcohol of general formula VIII $$HO-R_3 (ONO_2)_n \qquad (VIII)$$

in the presence of a condensation agent such as dicarbonyl diimidazole, dicyclohexyl carbodiimide, etc. in an aprotic, anhydrous inert organic solvent, such as chloroform, dichloromethane, tetrahydrofuran, etc. The ester obtained is finally disprotected by treatment with a hydroacid (J. Org. Chem. 43, 2285 (1978) in an aprotic, anhydrous, polar inert organic medium, such as for example ethyl acetate, tetrahydrofuran, etc, to give the general formula I compounds.

As stated above, the preferably used compounds of formula I are:

1-isopropylamino-3-[4-(2-nitroxy)ethoxymethyl]phenoxy-2-propanol, 1-isopropylamino-3-[4-(3-nitroxy)propoxymethyl]phenoxy-2-propanol, 1-isopropylamino-3-[4-(2,3-dinitroxy)propoxymethyl] phenoxy 2-propanol, 1-(2-hydroxy-3-isopropylamino)propoxy-N-(2-nitroxyethyl)-2-naphthalene acetamide, 2-(2-hydroxy-3-isopropylamino)propoxy-N-(2-nitroxyethyl)-1-naphthalene acetamide, 2-nitroxyethyl 4-[(2-hydroxy-3-isopropylamino)propoxy]phenyl acetate.

The synthesized products were subjected to a general pharmacological screening, by the application of a wide range of biological assays, to show potential activities of therapeutical interest. The coronary vasodilator and $\beta_1$ adrenergic blocking activities are outstanding among the results obtained.

The coronary vasodilator activity of the synthesized products was determined in vitro from their capacity to antagonize the contractions induced by a) potassium (35 mM) b) calcium (1.5 mM) and c) serotonin (1 mM) in helical strips of swine coronary artery, using Nitroglycerine and Nicorandil as reference drugs (Table 1).

In parallel tests, the effect of the said compounds on the positive isoprenaline-induced inotropic response in electrically stimulated isolated left auricle of the guinea pig, as evidence of $\beta_1$-adrenergic blocking activity (Table 2) was established. In this case, the reference drugs tested were Propranolol, Metoprolol and Atenolol.

TABLE 1

IN VITRO CORONARY VASODILATING ACTIVITY
Activity expressed as inhibitory concentration 50 ($IC_{50}$) en μM

| Drug | Effect on concentrations in swine coronary artery of | | |
|---|---|---|---|
| | $K^+$ (35 mM) | $Ca^{2+}$ (1.5 mM) | Serotonin (1 mM) |
| 2-nitroxyethyl 4-[(2-hydroxy-3-isopropyl-amino)propoxy]phenyl acetate | 0.3 | 13.1 | 5.7 |
| 1-isopropylamino-3-[4-(2-nitroxy) ethoxymethyl]phenoxy-2-propanol | 3.4 | N.S | 13.3 |
| 1-(2-hydroxy-3-isopropylamino)propoxy-N-(2-nitroxyethyl)-2-naphthalene acetamide | 40.7 | N.S | N.S |
| 2-(2-hydroxy-3-isopropylamino)propoxy-N-(2-nitroxyethyl)-1-naphthalene acetamide | 28.6 | 20% at 10 μM | 50% at 100 μM |
| 1-isopropylamino-3-[4-(2,3-dinitroxy) propoxymethyl]phenoxy-2-propanol | 0.5 | 1.7 | 1.6 |
| 1-isopropylamino-3-[4-(3-nitroxy) propoxymethyl]phenoxy-2-propanol | 7.1 | 50% at 30 μM | 6.0 |
| Nitroglycerine | 1.3 | 50% at 0.1 mM | 1.0 |
| Nicorandil | 49.7 | 169.0 | 14.7 |
| Propranolol | 98.6 | 72.4 | 8.1 |
| Metoprolol | 30% at 0.1 mM | N.S | 20% at 100 μM |
| Atenolol | 25% at 0.1 mM | N.S | N.S |

N.S. = Activity not significant

TABLE 2. $\beta_1$-ADRENERGIC BLOCKING ACTIVITY IN VITRO

Activity determined as antagonism of the isoprenaline-induced positive inotropic response in the electrically-stimulated isolated guinea pig left auricle, expressed as inhibitory concentration$_{50}$ (IC$_{50}$).

| Drug | IC$_{50}$ (μM) |
| --- | --- |
| 2-nitroxyethyl 4-[(2-hydroxy-3-isopropylamino)propoxy]phenyl acetate | 7.6 |
| 1-isopropylamino-3-[4-(2-nitroxy)ethoxymethyl]phenoxy-2-propanol | 0.6 |
| 1-(2-hydroxy-3-isopropylamino)propoxy-N-(2-nitroxyethyl)-2-naphthalene acetamide | N.S. |
| 2-(2-hydroxy-3-isopropylamino)propoxy-N-(2-nitroxyethyl)-1-naphthalene acetamide | 25% a 0.1 mM |
| 1-isopropylamino-3-[4-(2,3-dinitroxy)-propoxymethyl]phenoxy-2-propanol, | 4.8 |
| 1-isopropylamino-3-[4-(3-nitroxy)-propoxymethyl]phenoxy-2-propanol, | 0.7 |
| Propranolol | 1.8 |
| Metoprolol | 2.6 |
| Atenolol | 0.7 |

Activity not significant: N.S

Taking advantage of their coronary vasodilator properties and their $\beta_1$-adrenergic blocking action, the compounds of the invention may be used as drugs acting on the cardiocirculatory system in human therapy, particularly indicated in crises of angor, myocardial ischaemia, acute myocardial infarct, hypertension and arrhythmias.

They may be administered in the form of pharmacologically acceptable compositions, for example as tablets, coated tablets, retard tablets, capsules, syrups and suppositories. The soluble salts may be administered as injectables.

A number of non-limiting examples are given hereinafter to illustrate the inventive process.

EXAMPLE 1

1-isopropylamino-3-[4-(2-nitroxy)ethoxymethyl]phenoxy-2-propanol 1.840 g (0.008 mole) of 4-[(2-nitroxy)ethoxymethyl]phenol, dissolved in a mixture of 10.6 ml of ethanol and 10 ml (0.010 mole) of 1N NaOH, were added slowly to a solution of 15.970 g (13.5 ml, 0.172 mole) of epichlorohydrin in 7 ml of methanol. The mixture was stirred for 16 hours at room temperature. 50 ml of water were added and the mixture was concentrated at reduced pressure at 40° C. The residue was extracted with a mixture of 100 ml of ethyl acetate and 100 ml of water. It was decanted and the aqueous phase was extracted a further two times with 25 ml of ethyl acetate. The organic extracts were pooled and washed with 75 ml of 1N HCl and 75 ml of water. It was dried over anhydrous sodium sulphate, was filtered and was concentrated at reduced pressure. 2.030 g (0.007 mole) of 2,3-epoxy-1-[4-(2-nitroxy)ethoxymethyl]phenoxy propane were obtained in the form of a yellowish oil which was mixed with 4.476 g (6.45 ml, 0.075 mole) of isopropylamine in 25 ml of anhydrous methanol and was heated under reflux for two hours. It was concentrated at reduced pressure at 40° C. 100 ml of water were added and it was extracted three times with 50 ml of ethyl acetate. The organic extracts were pooled and extracted three times with 100 ml of 1N HCl. The acid extracts were pooled and were alkalized to pH=12 by addition of 1N NaOH. It was extracted four times with 50 ml of ethyl acetate. The extracts were pooled and washed with 60 ml of water. It was dried over anhydrous sodium sulphate, was filtered and the solvent was removed at reduced pressure until a constant weight was obtained. 1.714 g (61%) of the product were obtained in the form of an oil.

R$_f$=0.56 (TLC on silica gel Merck-5714, dioxane/acetonitrile/ 30% ammonium hydroxide/methanol: 60/36/5/4)

IR (CHCl$_3$) v$_{max}$: 3300 (broad band), 1630 (1605, 1580 back) 1500, 1275, 1240, 1100 and 850 cm$^{-1}$ $^1$H-NMR (CDCl$_3$)δ: 1,10 (d, 6H, J=6.3 Hz), 2.67–2.86 (m, 5H), 3.71 (m, 2H), 3.94–4.10 (m, 3H), 4.49 (s, 2H), 4.61 (m, 2H), 6.90 and 7.25 (dd AA' BB', 4H, J= 8.6 Hz)

$^{13}$C-NMR (CDCl$_3$) δ: 22.88, 22.97, 48.98, 49.27, 65.56, 68.35, 70.60, 72.17, 73.02, 114.56, 129.41, 129.72 and 158.54

EM impact (m/e, %): 329 (M$^+$=1, 12), 116 ([CH$_2$CHOHCH$_2$NHCH(CH$_3$)$_2$]$^+$, 28), 107 ([CH$_2$C$_6$H$_4$OH] $^+$, 23), 72 ([CH$_2$=NHCH(CH$_3$)$_2$]$^+$, 100)

EXAMPLE 2

1-isopropylamino-3-[4-(3-nitroxy)propoxymethyl]phenoxy-2-propanol 2.780 g (0.012 mole) of 4-[(3-nitroxy)propoxymethyl] phenol dissolved in a mixture of 15 ml of absolute ethanol and 4.2 ml (0.014 mole) of 1N NaOH were added slowly over a solution of 24.400 g (20.7 ml, 0.264 mole) of epichlorohydrin in 10.7 ml of absolute ethanol. The mixture was stirred at room temperature for 19 hours. 50 ml of water were added and the mixture was concentrated at reduced pressure at 40° C. The residue was extracted by stirring in a mixture of 150 ml of water and 150 ml of ethyl acetate. It was decanted and the aqueous phase was reextracted with a further 100 ml of ethyl acetate. The extracts were pooled and were washed twice with 250 ml of 1N HCl and a further two times with 250 ml of water. It was dried over sodium sulphate, was filtered and was concentrated to give 3.190 g of an oil which was purified by MPLC on silica gel (0.015–0.040 mm). The eluant was a mixture of CH$_2$Cl$_2$/acetone: 98/2 and the solvent was removed at reduced pressure until a constant weight was reached. 2.481 g (0.008 mole) of 2,3-epoxy-1-[4-[(3-nitroxy)propoxymethyl]phenoxy propane were obtained in the form of a yellow oil (R$_f$=0.76 TLC, silica gel Merck-5714, CHCl$_2$ acetone: 9/1), which was mixed with 5.192 g 7.48 ml, 0.088 mole) of isopropylamine in 30 ml of dry methanol and heated under reflux for 1 hour under anhydrous conditions. It was concentrated in the rotary evaporator with heating at 40° C. The oil obtained was extracted with 100 ml of ethyl acetate and 100 ml of water. It was decanted and the aqueous phase was treated with 50 ml of ethyl acetate. The organic phases were pooled and extracted twice with 100 ml of 1N HCl. The acid phases were pooled and were basified with 1N NaOH to pH=12. The mixture was extracted twice with 100 ml of ethyl acetate, the organic extracts were pooled and were washed with 100 ml of water. The product was dried over sodium sulphate. It was filtered and the solvent was removed at reduced pressure to give 2.156 g (51%) of a product in the form of a brown oil.

R$_f$=0.49 (TLC on silica gel Merck-5714, Dioxane/acetonitrile/NH$_4$ OH/methanol: 60/36/4/5)

IR (CHCl$_3$) V$_{max}$: 3350 (broad band), 1630 (1580 back), 1270 and 1240 cm$^{-1}$ $^1$H-NMR (CDCl$_3$) δ: 1.10 (d, 6H, J$_1$=6.2 Hz), 1.96–2.05 (m, 2H, J$_2$ =6.2 Hz, J$_3$=6.4 Hz), 2.61 (s broad, 2H, OH,NH), 2.65–2.95 (m, 3H), 3.53 (t, 2H, J$_2$= 6.2 Hz), 3.96–4.10 (m, 3H), 4.43 (s, 2H) 4.56 (t, 2H, $J_3$= 6.4 Hz), 6.90 and 7.24 (dd, AA'BB', 4H, $j_4$=8.8 Hz)

$^{13}$C-NMR (CDCl$_3$) δ: 22.83, 22.93, 27.40, 48.98, 49.19, 65.50, 68.34, 70.55, 72.77, 114.54, 129,30, 130,47, 158.42

EM chemical ionization (NH$_3$) (m/e, %): 343 (M$^+$+1, 100), 298 (M$^+$— (ONO$_2$)+18, 22)

EXAMPLE 3

1-isopropylamino-3-[4-(2,3-dinitroxy -propoxymethyl]phenoxy- 2-propanol 2.227 g (0.007 mole) of 4-[(2,3-dinitroxy)propoxymethyl]-phenol dissolved in a mixture of 10 ml of absolute ethanol and 9.46 ml (0.009 mole) of 1N NaOH were added slowly over a solution of 15.099 g (12.80 ml, 0.163 mole) of epichlorohydrin in 6.6 ml of absolute ethanol. The mixture was stirred at room temperature for 20 hours. 50 ml of distilled water were added and the mixture was concentrated at reduced pressure at 40° C. The residue was extracted by stirring in a mixture of 150 ml of water and 150 ml of ethyl acetate. It was decanted and the aqueous phase was washed a further two times with 50 ml of ethyl acetate. The organic extracts were pooled and were washed twice with 150 ml of 1N HCl and a further two times with 150 ml of water, followed by drying over sodium sulphate, filtering and removal of the solvent at low pressure. 2.214 g of a yellowish oil were obtained and were purified by MPLC on silica gel (0.015–0.040 mm). 1.750 g (0.005 mole) of 1,2-epoxy-3-[4-(2,3-dinitroxy)propoxy-methyl]phenoxy propane ($R_f$=0.56 TLC, silica gel Merck-5714, CH$_2$Cl$_2$/ acetone: 98/2) were recovered by eluting with a mixture of CH$_2$Cl$_2$/acetone: 98/2 and evaporating under vacuum. They were mixed with 4.496 g (6.48 ml, 0.076 mole) of isopropylamine in 22 ml of dry methanol and heated under reflux for 23 minutes under anhydrous conditions.

It was allowed to cool, 100 ml of dry methanol were added and it was concentrated in the rotary evaporator to give 1.840 g of a brown oil which was purified by MPLC over silica gel (0.015–0.040) and 0.934 g (30%) of the product in the form of a yellow oil were recovered on eluting with a mixture of ethyl acetate/methanol: 7:3 and removing the solvent at reduced pressure until a constant weight was obtained.

$R_f$=0.28 (TLC on Silica gel Merck-5714, ethyl acetate/ methanol: 7/3)

IR (CHCl$_3$) $v_{max}$: 3300 (broad band), 1654 (1612 and 1586 back) 1513, 1285, 1271, 1248, 1103 and 840 cm$^{-1}$ $^1$H-NMR (CDCl$_3$) δ: 1.11–1.14 (d, 6H $J_1$=6.2 Hz, 2.69–2.95 (m, 3H), 3.45 (s broad, 2H, OH,NH), 3.66–3.69 (d, 2H, $J_2$=5.0 Hz), 3.95–3.98 (m, 2H), 4.03–4.14 (m, 1H), 4.48 (s, 2H), 4.57–4.67 (dd, 1H, $J_3$ =6.6 Hz, $J_4$ = 12.8 HZ), 4.74–4.82 (dd, 1H, $J_5$=3.2 HZ, $J_4$=12.8 Hz), 5.34–5.44 (m, 1H), 6.90–7.22 (dd, AA'BB', 4H, $J_6$=8.6 Hz)

$^{13}$ C-NMR (CDCl$_3$) δ: 22.59, 49.12, 49.28, 66.08, 68.08, 69.25, 70.63, 73.34, 77.63, 114.61, 129.17, 129.59, 158,70

EM chemical ionization (NH$_3$), (m/e, %): 404 (M$^+$. 1.56 ), 359 ( M$^+$ —(ONO$_2$)+18, 38), 296 (M$^+$ —(2xONO$_2$)+18, 56), 240 (M$^+$ —(OCH$_2$CH(ONO$_2$)CH$_2$(ONO$_2$))+ 18, 100).

Preparation of
1-isopropylamino-3-[4-(2,3-dinitroxy)-propoxy -methyl]phenoxy- 2-propanol succinate 0.867 g (2.15·10$^{-3}$ mole) of 1-isopropylamino-3-[4-(2,3 -dinitroxy)-propoxymethyl]phenoxy-2-propanol were dissolved in 10 ml of acetone.

0.137 g (1.16·10$^{-3}$ mole) of succinic acid were added and the mixture was gently heated until the acid was dissolved.

It was allowed to cool to room temperature and then in a refrigerator until a white solid was formed.

Ether was added and the mixture was ground until a filterable fine powder was obtained. The ether was decanted off and this operation was repeated three times.

The product was filtered in a Büchner funnel to give 0.667 g (67% yield relative to the free base) of a white solid having a melting point of 104–6° C.

IR (KBr) $v_{max}$: 1643, 1614 (back), 1568, 1515, 1403, 1287, 1271, 1249, 841 cm$^{-1}$

EXAMPLE 4

1-(2-hydroxy-3-isopropylamino)propoxy-N -(2-nitroxyethyl)-2-naphthalene acetamide 4.600 g (0.015 mole) of 1-hydroxy-N(2-nitroxyethyl)-2-naphthalene acetamide dissolved in a mixture of 4 ml of water, 1.436 g (0.021 mole) of 85% potassium hydroxide and 38 ml of ethanol were added slowly over a solution of 35.490 g (30 ml, 0.383 mole) of epichlorohydrin in 17 ml of ethanol, with temperature control. The mixture was stirred at room temperature for 22 hours. 150 ml of water were added and the mixture was concentrated at reduced pressure at 40° C. The mixture was extracted three times with 70 ml of ethyl acetate and dried over sodium sulphate. It was filtered and the solvent was removed at low pressure. The oil obtained was purified by column chromatography in silica gel (0.060–0.200 mm). 2.354 g (0.006 mole) of 1-(2,3-epoxy)propoxy-N-(2- nitroxyethyl)- 2-naphthalene acetamide were obtained on eluting with a mixture of chloroform/ methanol: 9/1 and removing the solvent at reduced pressure (m.p. 67°–71° C., $R_f$=0.41 TLC, silica gel Merck HPTLC-5629, chloroform 80/acetone 20). They were mixed with 8.88 g (12.8 ml, 0.150 mole) of isopropylamine in 80 ml of methanol and heated under reflux for 1 hour under anhydrous conditions. The product was concentrated at reduced pressure at 40° C. The oil obtained was redissolved in 80 ml of ethyl acetate and was extracted three times with 35 ml of 1N HCl. The acid extracts were pooled and were alkalized with the addition of powdered sodium carbonate and a solution of 1N NaOH to pH=12. The solution was treated twice with 50 ml of ethyl acetate. The organic extracts were pooled and washed twice with 25 ml of sodium chloride saturated water. It was dried over anhydrous sodium sulphate, was filtered and was concentrated at reduced pressure to give a residue which was purified by column chromatography on silica gel (0.060–0.200 mm). On eluting with a mixture of chloroform 90/methanol 20 and removing the solvent at reduced pressure until a constant weight, 1.113 g (17%) of an oil which solidified in amorphous form were obtained.

$R_f$=0.59 TLC on silica gel Merck HPTLC-5629 eluted with ethanol/acetone/acetic acid: 8/2/2

IR (film) $v_{max}$: 3420–3150, 1665, 1640 and 1281 cm$^{-1}$

1H-NMR (CDCl$_3$) δ: 1.38–1.42 (d, 6H, $J_1$=6.26 Hz), 3.0–3.39 (m, 9H), 4.0 (m, 2H), 4.42–4.47 (t, 2H, $J_2$ =5.12 Hz), 4.60 (s, 1H), 7.30–7.40 (m, 2H), 7.50–7.62 (m, 2H), 7.70–7.79 (m, 1H), 7.88–7.95 (m, 1H)

$^{13}$C-NMR (CDCl$_3$) δ: 172.19, 151.81, 134.30, 128,61, 128.14, 127.66, 126.35, 126.10, 124.91, 123.92, 121.48, 75.81, 71.64, 66.40, 51.46, 47.57, 37.50 and 36.89

EM (impact) (m/e, %): 43 ((CH$_3$)$_2$CH)$^+$, 35.4), 72 ((CH$_2$=NH CH(CH$_3$)$^+$, 47.9), 156 (C$_1$OH$_6$O)$^+$, 15.5), 227 (OC$_1$OH$_6$CH$_2$—CONH CH$_2$CH$_2$)$^+$, 100)

EXAMPLE 5

2-(2-hydroxy-3-isopropylamino)propoxy-N-(2-nitroxyethyl)-1-naphthalene acetamide 5.326 g (0.018 mole) of 2-hydroxy-N-(2-nitroxyethyl)-1-naphthalene acetamide were mixed with 31.4 ml of 1N sodium hydroxide, 31.4 ml of water and 70.980 g (60 ml, 0.767 mole) of epichlorohydrin. The mixture was stirred at room temperature for 24 hours. 100 ml of ethyl acetate were added, the mixture was stirred and decanted. The organic phase was taken, was washed with 50 ml of 0.1 N NaOH, was dried over anhydrous sodium sulphate and was concentrated to dryness under reduced pressure. The residue obtained was extracted with stirring in 50 ml of isopropanol. It was concentrated at reduced pressure and the resulting oil was redissolved in 100 ml of anhydrous methanol. It was mixed with 69.400 g (100 ml, 1.174 mole) of isopropylamine. It was heated under reflux for 1.5 hours. The solvent was removed by evaporation and the residue was redissolved in 100 ml of ethyl acetate. It was cooled to +5° C. and extracted four times in 45 ml of 0.1 N HCl. The aqueous phases were pooled and were basified at +5° C. by addition of powdered sodium carbonate and 1N NaOH solution to pH=11. It was extracted five times with 40 ml of ethyl acetate. The extracts were pooled and washed with 60 ml of sodium chloride saturated water and were dried over anhydrous sodium sulphate. The mixture was filtered and the solvent was removed at reduced pressure. The residue was purified by column chromatography on silica gel (0.2–0.06 mm). The fraction eluted with ethyl acetate/methanol: 100/5 and concentrated at reduced pressure gave an oil crystallizing on stirring with 10 ml of acetone to obtain 1.508 g (20%) of product (m.p. 129–132° C.).

R$_f$=0.50 (TLC on silica gel Merck-5714 eluted with dioxane/acetonitrile/methanol/ 30% ammonium hydroxide 60/36/4/5)

IR (KBr) $v_{max}$: 1645, 1630, 1600, 1565, 1390, 1285 and 1255 cm$^{-1}$

EXAMPLE 6

2-nitroxyethyl 4-[(2-hydroxy-3-isopropylamino)propoxy]phenyl acetate 1.444 g (4 mmoles) of 4-[[2-hydroxy-3-N-(t-butyloxycarbonyl)isopropylamino]propoxy]phenylacetic acid were added to a solution of 0.637 g (3.9 mmoles) of 1-1'-carbonyldiimidazole in 50 ml of anhydrous dichloromethane under a dry nitrogen atmosphere. The mixture was stirred for 10 minutes and 1.700 g (1.6 mmoles) of 2-nitroxyethanol dissolved in 100 ml of dichloromethane.

Finally, the mixture was stirred for 10 hours. It was washed twice with 20 ml of a 1N HCl solution, was buffered by washing with a 5% sodium bicarbonate solution and was dried over anhydrous sodium sulphate. It was filtered and the solvent was removed at reduced pressure, to give an oil which was purified by column chromatography on silica gel (0.063–0.200 mm). On eluting with a mixture of chloroform/acetone: 95/5 and removing the solvent by evaporation at reduced pressure until constant weight, 0,950 g (2 mmoles) of 2-nitroxyethyl 4-[[2-hydroxy-3-N-(t-butyloxycarbonyl)-isopropylamino)propoxy]phenyl acetate were obtained in form of an oil (R$_f$= 0.52 TLC Silica gel Merck HPTLC-5629, chloroform/acetone: 80/20), which were dissolved in 2.4 ml (7.2 mmoles) of 3N HCl solution in anhydrous ethyl acetate, with cooling to +5° C. The temperature was allowed to rise to room temperature with stirring for 30 minutes. 20 ml of ethyl acetate were added and the mixture was washed twice more with 10 ml of 1N NaOH solution, was buffered by washing twice with sodium chloride saturated water and was dried over anhydrous sodium sulphate. It was filtered and the solvent was removed at reduced pressure until a constant weight was obtained, to give 0.515 g (36%) of the product in the form of a colorless oil which crystallized (m.p. 44–47° C., white crystals).

I.R. (film) $v_{max}$: 3500–2700 (max at 3289 and 2967), 1742, 1633, 1514, 1281, 1248, 1159, 1025 and 854 cm$^{-1}$.

$^1$H-NMR (CDCl$_3$) δ: 1.1 (d, 6H, J$_1$=6.3 Hz), 2.65–2.75 (dd, 1H J$_2$=12.2 J$_3$=7.1) 2.75–2.95 (m, 2H), 3.1 (s (broad), 2H ), 3.57 (s, 2H), 3.94 (d, 2H, J$_4$=5.8 Hz), 4.05 (m, 1H), 4.31–4.36 (m, 2H), 4.60–4.65 (m, 2H) 6.85 and 7.17 (AA' BB', dd, 4H J=8.6 Hz)

$^{13}$C-NMR (CDCl$_3$) δ: 171.5, 157.9, 130.3, 125.7, 114.7, 70.4, 70.3, 68.5, 60.5, 49.1, 49.0, 40.0, 22.8 and 22.7.

EM (impact)(m/e, %) : 46 ([NO$_2$]$^+$, 3.1), 72 ([CH$_2$=NHCH(CH$_3$)$_2$ ]$^+$, 100), 107 ([CH$_2$C$_6$H$_4$OH]$^+$, 7) 116 ([CH$_2$CHOHCH$_2$NHCH (CH$_3$)$_2$]$^+$, 7.1)

EXAMPLE A

Preparation of the Galenic Form of Tablets (1) Composition:

| | |
|---|---|
| 2-nitroxyethyl 4-[(2-hydroxy-3-isopropylamino)propoxy]phenyl acetate | 50 mg |
| Avicel PH 102 SCG | 50 mg |
| Starch 1500 | 25 mg |
| Talc | 10 mg |
| Precirol AT05 | 2 mg |

(2) Preparation:

The 2-nitroxyethyl 4-[(2-hydroxy-3-isopropylamino)propoxy]phenyl acetate, Avicel PH 102 SCG and starch 1500 were blended for 25 minutes, after having been sifted through a sieve of 0.5 mm diameter mesh.

The talc and the Precirol ATO5 were added, after having been sifted through a 0.5 mm mesh sieve for 5–10 minutes.

The tablets were pressed in a rotary machine to a theoretical weight of 137 mg with a 8 mm diam. double concave punch.

EXAMPLE B

Preparation of the Galenic Form of Retard Tablets (1) Composition:

| | |
|---|---|
| 2-(2-hydroxy-3-isopropylamino)propoxy-N-(2-nitroxyethyl)-1-naphthalene acetamide | 50 mg |
| Ground sugar | 60 mg |
| Plasdone | 20 mg |
| Talc | 5 mg |
| Precirol AT05 | 15 mg |

(2) Preparation:

The 2-(2-hydroxy-3-isopropylamino)propoxy-N-(2-nitroxyethyl)-1-naphthalene acetamide and ground sugar were blended for 25 minutes, after having been sifted through a sieve of 0.5 mm diameter mesh.

A hydroalcoholic suspension of Plasdone and Precirol ATO5 was added to the resulting mixture, with kneading until an appropriate consistency was obtained. It was granulated through a 3 mm diameter mesh sieve and dried in a fluidized bed at 60°. It was ground, sifted through 0.7 mm mesh and blended with the talc.

The tablets were pressed in a rotary machine to a theoretical weight of 150 mg with a 10 mm diam. double concave punch.

EXAMPLE C

Preparation of the Galenic Form of Capsules (1) Composition:

| | |
|---|---|
| 1-isopropylamino-3-[4-(2,3-dinitroxy)- propoxymethyl]phenoxy-2-propanol | 50 mg |
| Lactose | 400 mg |
| Magnesium stearate | 5 mg |

(2) Preparation:

The 1-isopropylamino-3-[4-(2,3-dinitroxy)-propoxymethyl]phenoxy-2-propanol and lactose were blended for 25 minutes, after having been sifted through a sieve of 5 μm mesh.

Hard gelatine capsules with a theoretical content of 455 mg each were filled with the mixture obtained.

EXAMPLE D

Preparation of the Galenic Form of Injectables (1) Composition:

| | |
|---|---|
| 1-isopropylamino-3-[4-(2,3-dinitroxy)- propoxymethyl]phenoxy-2-propanol | 50 mg |
| 0.2 m pH 7.4 phosphates buffer | 2 ml |

The 1-isopropylamino-3-[4-(2,3-dinitroxy)propoxymethyl]phenoxy-2-propanol was mixed in the 0.2 m pH 7.4 phosphates buffer in the previously set proportion.

The mixture was stirred until complete dissolution and was filtered through a 0.2 sterile filter.

Topaz glass vials were filled to a theoretical content of 2 ml each with the filtered liquid.

What we claim is:

1. 1-aryloxy-3-alkylamino-2-propanol nitrate esters of general formula I $$R_1-Ar-O-CH_2-\underset{\underset{OH}{|}}{CH}-CH_2-NH-CH(CH_3)_2 \qquad (I)$$

and the enantiomers and diastereoisomers and therapeutically acceptable organic and inorganic acid salts thereof: where
$R_1$ is a chain of general formula II $$-(CH)_m-Z-R_2 \qquad (II)$$

where m is 1 or 2; Z is a $-C(O)NH$-amide; and $R_2$ is a $C_{2-3}$ straight or branched chain alkyl having at least one-$ONO_2$ group as a substituent; and Ar is a naphthalene ring.

2. A pharmaceutical composition comprising a therapeutically effective amount of at least one of the compounds according to claim 1, produced in a form selected from the group consisting of tablets, retard tablets, capsules and injectables.

3. Nitrate esters of general formula I, according to claim 1, selected from the group consisting of 1-(2-hydroxy-3-isopropylamino)propoxy-N-( 2-nitroxyethyl)-2-naphthalene acetamide and 2-(2-hydroxy-3-isopropylamino)propoxy-N-(2-nitroxyethyl)-1-naphthalene acetamide.

* * * * *